(12) United States Patent
Lim et al.

(10) Patent No.: US 11,168,412 B2
(45) Date of Patent: *Nov. 9, 2021

(54) FACILE METHODS FOR FABRICATING A UNIFORMLY PATTERNED AND POROUS NANOFIBROUS SCAFFOLD

(71) Applicants: Dong Jin Lim, Birgmingham, AL (US); Jeremy Vines, Birmingham, AL (US)

(72) Inventors: Dong Jin Lim, Birgmingham, AL (US); Jeremy Vines, Birmingham, AL (US)

( * ) Notice: Subject to any disclaimer, the term of this patent is extended or adjusted under 35 U.S.C. 154(b) by 593 days.

This patent is subject to a terminal disclaimer.

(21) Appl. No.: 15/967,597

(22) Filed: Apr. 30, 2018

(65) Prior Publication Data
US 2018/0274130 A1 Sep. 27, 2018

Related U.S. Application Data

(63) Continuation-in-part of application No. 14/663,316, filed on Mar. 19, 2015, now Pat. No. 9,956,711.
(Continued)

(51) Int. Cl.
*D01D 5/00* (2006.01)
*A61L 27/38* (2006.01)
(Continued)

(52) U.S. Cl.
CPC ............ *D01D 5/0076* (2013.01); *A61L 27/16* (2013.01); *A61L 27/18* (2013.01); *A61L 27/38* (2013.01); *A61L 27/3834* (2013.01); *A61L 27/48* (2013.01); *A61L 27/54* (2013.01); *A61L 27/56* (2013.01); *A61L 27/58* (2013.01); *A61L 2300/412* (2013.01); *A61L 2300/64* (2013.01);
(Continued)

(58) Field of Classification Search
CPC ............. D01D 5/0076; D01B 2211/06; D01B 2509/00; A61L 27/16; A61L 27/18; A61L 27/38; A61L 27/54; A61L 27/56; A61L 27/58; A61L 27/3834; A51L 2300/412; A51L 2300/64
USPC ........................................................ 264/413
See application file for complete search history.

(56) References Cited

U.S. PATENT DOCUMENTS

| | | | |
|---|---|---|---|
| 9,253,890 B2 * | 2/2016 | Chang | ...................... H05K 3/02 |
| 2008/0220042 A1 | 9/2008 | Hashi et al. | |
| 2009/0220605 A1 * | 9/2009 | Wei | ..................... A61L 27/3608 424/486 |

OTHER PUBLICATIONS

Tsang VL, Bhatia SN. Three-dimensional tissue fabrication. Advanced drug delivery reviews 2004;56:1635-47.
(Continued)

*Primary Examiner* — Jeffrey M Wollschlager
*Assistant Examiner* — Xue H Liu

(57) ABSTRACT

This invention describes a modified electrospinning method for making uniformly patterned and porous nanofibrous scaffolds that can be utilized in a variety of applications. While traditional electrospinning method uses a foil collector that generates compact layers of nanofibrous structures, resulting on the superficial cell growth and differentiation, the present method comprises adopting additional patterned film(s) on top of the conventional collector to make a patterned porous structure of nanofibrous scaffolds that are capable of supporting cell growth. For example, the method uses a double layered collector composed of a water soluble stabilizer film mounted on a foil to make a uniformly patterned and porous nanofibrous membrane sheets, which enhance both cell growth and attachment.

11 Claims, 11 Drawing Sheets

Related U.S. Application Data

(60) Provisional application No. 61/955,343, filed on Mar. 19, 2014.

(51) Int. Cl.
| | |
|---|---|
| A61L 27/18 | (2006.01) |
| A61L 27/56 | (2006.01) |
| A61L 27/58 | (2006.01) |
| A61L 27/54 | (2006.01) |
| A61L 27/16 | (2006.01) |
| A61L 27/48 | (2006.01) |

(52) U.S. Cl.
CPC ....... *A61L 2400/12* (2013.01); *D10B 2211/06* (2013.01); *D10B 2509/00* (2013.01)

(56) References Cited

OTHER PUBLICATIONS

Hollister SJ. Porous scaffold design for tissue engineering. Nature materials 2005;4:518-24.
Karageorgiou V, Kaplan D. Porosity of 3D biomaterial scaffolds and osteogenesis. Biomaterials 2005;26:5474-91.
Yang S, Leong KF, Du Z, Chua CK. The design of scaffolds for use in tissue engineering. Part I. Traditional factors. Tissue engineering 2001;7:679-89.
Mikos AG, Temenoff JS. Formation of highly porous biodegradable scaffolds for tissue engineering2000.
Tang ZG, Black RA, Curran JM, Hunt JA, Rhodes NP, Williams DF. Surface properties and biocompatibility of solvent-cast poly[caprolactone] films. Biomaterials 2004;25:4741-8.
Lu L, Peter SJ, Lyman MD, Lai HL, Leite SM, Tamada JA, et al. In vitro degradation of porous poly(L-lactic acid) foams. Biomaterials 2000;21:1595-605.
Nam YS, Yoon JJ, Park TG. A novel fabrication method of macroporous biodegradable polymer scaffolds using gas foaming salt as a porogen additive. Journal of biomedical materials research 2000;53:1-7.
Whang K, Thomas CH, Healy KE, Nuber G. A novel method to fabricate bioabsorbable scaffolds. Polymer 1995;36:837-42.
Peltola SM, Melchels FP, Grijpma DW, Kellomaki M. A review of rapid prototyping techniques for tissue engineering purposes. Annals of medicine 2008;40:268-80.
Teo WE, Ramakrishna S. A review on electrospinning design and nanofibre assemblies. Nanotechnology 2006;17:R89-R106.
Wright LD, Andric T, Freeman JW. Utilizing NaCl to increase the porosity of electrospun materials. Materials Science and Engineering: C 2011;31:30-6.
Buser D, Dula K, Belser U, Hirt HP, Berthold H. Localized ridge augmentation using guided bone regeneration. 1. Surgical procedure in the maxilla. Int J Periodontics Restorative Dent 1993;13:29-45.
Nyman S, Lindhe J, Karring T, Rylander H. New attachment following surgical treatment of human periodontal disease. J Clin Periodontol 1982;9:290-6.
Gottlow J, Nyman S, Karring T, Lindhe J. New attachment formation as the result of controlled tissue regeneration. J Clin Periodontol 1984;11:494-503.
Dahlin C, Linde A, Gottlow J, Nyman S. Healing of bone defects by guided tissue regeneration. Plast Reconstr Surg 1988;81:672-6.
Murphy KG. Postoperative healing complications associated with Gore-Tex Periodontal Material. Part I. Incidence and characterization. Int J Periodontics Restorative Dent 1995;15:363-75.
Simion M, Scarano A, Gionso L, Piattelli A. Guided bone regeneration using resorbable and nonresorbable membranes: a comparative histologic study in humans. Int J Oral Maxillofac Implants 1996;11:735-42.
Fujihara K, Kotaki M, Ramakrishna S. Guided bone regeneration membrane made of polycaprolactone/calcium carbonate composite nano-fibers. Biomaterials 2005;26:4139-47.
Taguchi Y, Amizuka N, Nakadate M, Ohnishi H, Fujii N, Oda K, et al. A histological evaluation for guided bone regeneration induced by a collagenous membrane. Biomaterials 2005;26:6158-66.
Scantlebury TV. 1982-1992: a decade of technology development for guided tissue regeneration. J Periodontol 1993;64:1129-37.
Gentile P, Chiono V, Tonda-Turo C, Ferreira AM, Ciardelli G. Polymeric membranes for guided bone regeneration. Biotechnology Journal 2011;6:1187-97.
Zhao S, Zhou Q, Long YZ, Sun GH, Zhang Y. Nanofibrous patterns by direct electrospinning of nanofibers onto topographically structured non-conductive substrates. Nanoscale 2013;5:4993-5000.
Gimble JM, Katz AJ, Bunnell BA. Adipose-derived stem cells for regenerative medicine. Circulation research 2007;100:1249-60.
Kulangara K, Leong KW. Substrate topography shapes cell function. Soft Matter 2009;5:4072-6.
Schwarz US, Bischofs IB. Physical determinants of cell organization in soft media. Med Eng Phys 2005;27:763-72.
Kim TG, Chung HJ and Park TG. Macroporous and nanofibrous hyaluronic acid/collagen hybrid scaffold fabricated by concurrent electrospinning and deposition/leaching of salt particles. Acta Biomater. 2008;4:1611-9.
Li J, He A, Zheng J and Han CC. Gelatin and gelatin-hyaluronic acid nanofibrous membranes produced by electrospinning of their aqueous solutions. Biomacromolecules 2006;7:2243-7.
Buttafoco L, Kolkman NG, Engbers-Buijtenhuijs P, Root AA, Dijkstra PJ, Vermes I and Feijen J. Electrospinning of collagen and elastin for tissue engineering applications. Biomaterials 2006;27:724-34.
Matthews JA, Wnek GE, Simpson DG and Bowlin GL. Electrospinning of collagen nanofibers. Biomacromolecules. 2002;3:232-8.
Fischer RL, McCoy MG and Grant SA. Electrospinning collagen and hyaluronic acid nanofiber meshes. J Mater Sci Mater Med. 2012;23:1645-54.
Elmaparithi A, Punnoose AM and Kuruvilla S. Electrospun type 1 collagen matrices preserving native ultrastructure using benign binary solvent for cardiac tissue engineering. Artif Cells Nanomed Biotechnol. 2016;44:1318-25.
Dong B, Arnoult O, Smith ME and Wnek GE. Electrospinning of collagen nanofiber scaffolds from benign solvents. Macromol Rapid Commun. 2009;30:539-42.
Pluke et al. Florida Entomologist, 2005.

\* cited by examiner (A)

(B)

(C)

FACILE METHODS FOR FABRICATING A UNIFORMLY PATTERNED AND POROUS NANOFIBROUS SCAFFOLD

The current application is a continuation-in-part (CIP) application of a U.S. non-provisional application Ser. No. 14/663,316 filed on Mar. 19, 2015.

FIELD OF INVENTION

The present invention relates to the fabrication of a uniformly patterned and porous nanofibrous scaffold for tissue engineering. The present invention describes a facile method for making uniformly patterned and porous nanofibrous membranes that can be utilized in a variety of applications. For example, in one embodiment, to prepare a microenvironment for incorporating cells, bioactive molecules, and therapeutic materials. This invention can be fabricated in such a way as to modify parameters such as elasticity, flexibility and porosity of given materials, which are critical components for making a natural mimic environment for tissue engineering and other similar applications such as cosmetics and pharmaceutics.

BACKGROUND OF THE INVENTION

A growing body of studies developing and investigating three-dimensional scaffolds have proven that biophysical parameters are an essential factor necessary to mimic the cellular environment, allowing for the regeneration of tissues and organs [1, 2]. While mechanically supporting cellular environments, three-dimensional scaffolds are often designed with porous and interconnected networks that guide cellular behaviors, resulting in successful tissue and organ regeneration [3]. Porous structures within a biomaterial are capable of nurturing, growing, and differentiating cells, contributing to improved tissue regeneration [4]. In the field of tissue engineering, there have been many attempts to make three-dimensional scaffolds that allow cell growth and tissue regeneration. For example, solvent casting, particle leaching, gas foaming, and melt molding have all been proposed. Additionally, rapid prototyping systems have also been considered in order to control the size, pore geometry, and interconnectivity of scaffolds. Common rapid prototyping systems utilize selective laser sintering (SLS), fused deposition modeling (FDM), stereolithography (SLA), 3D printing as well as 3D plotting to generate scaffolds [5-10]. However, one of the most studied and popular methods for fabricating scaffolds is electrospinning. Electrospinning has been widely applied to the fabrication of biomimetic scaffold that remodels the native extracellular matrix (ECM) [11]. Conventional electrospinning is an easy and commonly utilized method for the fabrication of nanofibrous polymer scaffolds that are capable of supporting cell growth.

Traditional electrospinning employs a conductive collector that is set some distance away from a syringe containing a polymer solution. Both the syringe and the collector are hooked up to a high voltage source, with the positive charge connected to the syringe and the ground connected to the collector, generating a voltage differential. When a high voltage is applied to the collector and the syringe, the polymer overcomes the surface tension of the syringe and is deposited on the collector in a nanofiber configuration. The resulting electrospun scaffolds are composed of nanofibrous layers arranged in a tightly packed conformation.

However, traditional electrospinning methods are limited in the sense that they are not capable of fabricating porous scaffolds to allow the infiltration of cells without additional modification. Many attempts have been made to make a porous scaffold with consistency, but the majority of these methods are labor intensive and do not result in consistent porous structures. In fact, most methods require extra handling steps and produce patterning and porosity that is unpredictable and random. For example, one such method involves the incorporation of a water soluble material such as salt into the polymer solution. During the electrospinning process, the salt is deposited into the polymer fibers and incorporated into the scaffold. Following formation of the nanofibrous sheet, it is submerged into water in order to leach the salt out, leaving behind porous defects [12]. However, these porous defects are not interconnected throughout the scaffold and are simply pouches that allow cell populations to form enclaves within the scaffold. Furthermore, these porous defects do not allow cells to grow throughout the scaffold.

One example where electrospun scaffolds may be beneficial is in guided bone regeneration (GBR). GBR is a clinically proven technique used to restore maxillofacial defects using barrier membranes to cover the defects and induce bone regeneration [13]. In this regard, the membrane is intended to prevent soft-tissue ingrowth into the bone defect while promoting bone tissue regeneration [14, 15]. The osteoinductive space created by a membrane sheet enables bone formation around the periodontal defect with successful prevention of gingival connective tissue invasion, which can hinder osteoinduction. Dahlin et al. used a porous polytetrafluoroethylene (PTFE) membrane to facilitate the migration of cells responsible for osteogenesis to the defect site within the mandibular angles of Sprague-Dawley rats [16]. Although PTFE's biological inertness is a beneficial property for vascular grafts, the use of such non-resorbable materials often leads to postoperative healing complications [17]. For this reason, a second surgical manipulation to remove the non-resorbable membrane after 4 to 6 weeks following the initial operation is unavoidable.

Unlike traditional PTFE membranes, resorbable membranes do not require a secondary surgical manipulation, leading to successful GBR with reduced patient discomfort. In general, two types of materials have been studied for use as resorbable membranes: synthetic resorbable membranes and naturally biodegradable membranes.

Poly(glycolic acid) (PGA), poly(lactic acid) (PLA), poly (ε-caprolactone) (PCL), and their copolymers are the most commonly used materials for synthetic resorbable membranes, whereas bovine and porcine collagen membranes are commercially available, naturally biodedgradable materials used for GBR [18, 19, 20]. All resorbable membranes have previously been modified and reinforced in order to meet essential features necessary for successful GBR. These features include biocompatibility, selective cell ingrowth for bone regeneration, space maintenance, mechanical stability, adequate degradability, good tissue integration, and ease of use [21]. Of these characteristics, selective cell ingrowth following migration is a critical parameter necessary to facilitate the migration of osteogenic cells while retarding the ingrowth of gingival connective tissue. This feat is usually achieved via the utilization of a multi-layered membrane [22]. For instance, Epi-Guide®, which is a porous membrane made from three layers of a poly-D, DL, L-lactic acid polymer, retains fibroblasts and epithelial cells within the membrane while the layered barrier membrane allows bone regeneration by maintaining space around the defect up to 20 weeks. Another example is Bio-Gide®, which is a bi-layered membrane made of a non-cross-linked collagen membrane. The compact layer of this membrane provides a protective barrier for adjacent connective tissue while the porous layer supports bone and periodontal regeneration. Hence, for successful GBR, the generation of a porous structure without sophisticated methodologies would be preferred. Ideally, a technique that enables the production of a selective, patterned porous structure within the multi-layered membrane would have great potential for use in resorbable membranes for GBR. Thus, this invention involves a novel electrospinning technique in which a modified collector apparatus is used to provide a much less demanding process for the fabrication of a uniformly patterned and porous nanofibrous structure within a resorbable GBR membrane.

SUMMARY OF THE INVENTION

This invention describes a modified electrospinning method to make uniformly patterned and porous nanofibrous scaffolds. The method comprises of utilizing a double layered collector composed of a water soluble, organic-solvent soluble, or pyro-lytic or melt-able film mounted on a foil. While traditional electrospinning methods use a foil collector that generates compact layers of nanofibrous structures, resulting in superficial cell growth and differentiation, the present method comprises adopting additional patterned film(s) on top of the conventional collector to make a patterned porous structure of nanofibrous scaffolds that are capable of supporting cell growth. For example, the method uses a double layered collector composed of a water, organic-solvent soluble, or pyro-lytic or melt-able stabilizer film mounted on a foil to make a uniformly patterned and porous nanofibrous membrane sheets, which enhance both cell growth and attachment. The presence of these structures was confirmed by scanning electron microscope (SEM) (FIGS. 2 and 3). Cellular attachment and proliferation were examined within the fabricated sheets using human adipose-derived stem cells (hASCs) (FIG. 5). Compared to electrospun sheets prepared by a conventional collector, the patterned and porous sheets significantly improved hASC ingrowth. Enhanced hASC attachment and proliferation were also confirmed by total cellular proliferation activity and SEM (FIGS. 6 and 7). These results indicated that the facile membrane fabrication method described in this study is a promising approach to prepare a porous membrane for periodontal regeneration applications such as GBR.

In one aspect, the invention provides a method of producing a uniformly patterned and porous nanofiber scaffold utilizing a modified electrospinning technique, wherein the modification comprises a double layered collector composed of a water soluble, organic solvent, or pyro-lytic or melt-able soluble film mounted on a foil, the method comprising:
 a) adding a solution comprising a polymer into a syringe;
 b) connecting a positive charge to the syringe and the collector to the ground, and generating a voltage differential;
 c) applying a voltage to the collector and the syringe to allow the polymer to overcome the surface tension of the syringe and be deposited on the collector in a nanofiber configuration; and
 d) isolating the nanofibrous polymer structure.

wherein the water soluble film mounted on the foil can be a water soluble polymer structure, and the polymer in the syringe can be an organic solvent soluble polymer; and wherein the water soluble polymer film, which can be, but is not limited to any water soluble film such as an embroidery water soluble stabilizer film (EWS) provided by Sulky (Kennesaw, Ga., USA) or solvy water soluble stabilizer film (SWS) provided by Vilene;

wherein the organic solvent soluble film mounted on the foil can be an organic solvent soluble polymer structure, and the polymer in the syringe can be a water soluble polymer;

wherein the polymer in the syringe can be a water soluble or organic soluble polymer; and the pyro-lytic or melt-able film mounted on the foil can be a pyro-lytic or melt-able structure with a lower melting temperature than the polymer in the syringe.

wherein the polymer in the syringe is a synthetic or natural polymer or in combination thereof; wherein the synthetic polymer can be, but is not limited to polylactic acid (PLA), polyglycolic acid (PGA), poly-L-lactic acid (PLLA), poly(D, L-lactic-co-glycolic acid), (poly(D, L-lactide-co-glycolide); PLGA), poly(caprolactone) (PCL), diol/di acid-based aliphatic polyester, polyester-amide/polyester-urethane, aliphatic polyester of poly(valerolactone), poly(hydroxybutyrate) and poly(hydroxyl-valerate); wherein the natural polymer can be, but is not limited to collagen, fibronectin, alginate, hyaluronic acid, and other extracellular matrix proteins;

wherein the solution comprising a polymer in the syringe can further comprise inorganic molecules selected from the group consisting of salt, hydroxyapatite, tricalcium phosphate, tetracalcium phosphate, and various other metallic ions and ceramic molecules; and wherein the solution in the syringe can comprise collagen, polycaprolactone and hydroxyapatite; and wherein the uniformly patterned and porous nanofiber scaffold can be nanofibrous membrane sheets.

In another aspect, the invention provides a method of producing a uniformly patterned and porous nanofiber scaffold utilizing a modified electrospinning technique, wherein the modification comprises a double layered collector composed of a water soluble or an organic solvent soluble film mounted on a foil, wherein the nanofibrous membrane sheets produced are further seeded with cells, wherein the cells attached on the nanofibrous membrane sheets can be, but are not limited to human adipose-derived stem cells (hASCs) or another cell type such as human bone marrow mesenchymal stem cells (hMSCs), among others.

In another aspect, the method can be modified to generate uniformly patterned and porous nanofiber scaffolds that are three dimensional in nature, wherein the patterned scaffold is three dimensional instead of in a two dimensional sheet formation.

In another aspect, the method can be modified to generate layered scaffolds by stacking additional layers of water soluble films on top of one layer of electrospun scaffold and then electro spun an additional time to generate multiple layers of biomaterial.

Natural polymers such as collagen, elastin, fibronectin, and hyaluronic acid have been utilized in various electrospinning applications both by themselves and in tandem with regular synthetic polymers [27, 28, 29, 30]. For example, it is possible to electrospin collagen nanofibers via solubilization of collagen in specialized solutions such as HFIP, trifluoroethanol, hypertonic salt solutions, and high concentrations of acetic acid [31, 32, 33], following which, commonly used electrospinning setups can be used.

However, considering that the general principle for electrospinning these natural polymers is the same as that employed in the electrospinning of synthetic polymers such as polycaprolactone and plga, they also suffer from the same limitations in terms of fiber density and the lack of sufficient porosity for cellular ingrowth.

DETAILED DESCRIPTIONS OF THE INVENTION

Figure 1:
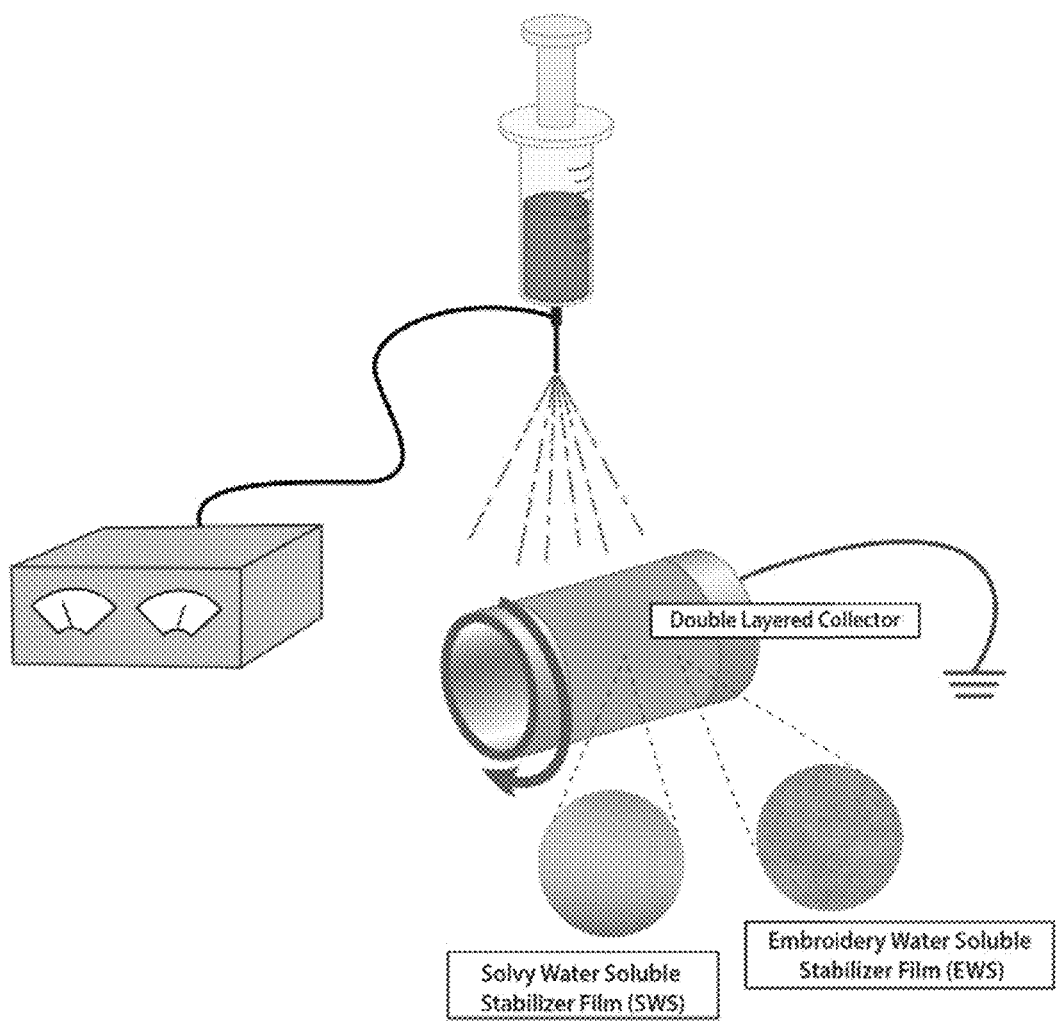
FIG. 1 describes general schematic drawing of the modified electrospinning apparatus. The key distinction is the incorporation of an additional water, or organic-solvent soluble patterned film on top of the metal collector, wherein the water soluble patterned film can be an embroidery water soluble stabilizer film (EWS) or a solvy water soluble stabilizer film (SWS).

The present invention relates generally to a porous nanofibrous membrane sheet for biomedical application and a facile method of preparing such uniformly patterned and porous nanofibrous membranes. While traditional electrospinning uses a foil collector that generates compacted layers of nanofibrous structures, resulting in the superficial cell growth and differentiation, the present invention adopts additional sheet(s) on the top of the conventional collector to make a patterned porous structure. The present invention uses a double layered collector system composing of a flat aluminum foil and a patterned water soluble stabilizer film. The water soluble stabilizer film enables the formation of uniformly patterned structures while nanofibers mount onto a conventional collector during electrospinning (FIG. 1). In different embodiments of the present invention, the properties and types of additional sheet(s) may vary.

In one embodiment, a water soluble film with an organic-solvent soluble polymer on top of the film may be used. In another embodiment, an organic-solvent soluble film with a water soluble polymer on top of the film may be used. In another embodiment, a pyro-lytic or melt-able film with a lower melting temperature than the polymer on top of the film may be used. By using polymers and patterned films with varying properties, different types of materials may be prepared. For example, a rapidly water dissolvable nanofibrous scaffold may be made by electrospinning a water soluble material on top of an organic-solvent soluble film and dissolving the film with an organic solvent.

In another embodiment, the method can be modified to generate uniformly patterned and porous nanofiber scaffolds that are three dimensional in nature, wherein the patterned scaffold is three dimensional instead of in a two dimensional sheet formation. This could be generated by wrapping a water or an organic solvent soluble film around a three dimensional frame and then electrospinning on top of the frame.

In another embodiment, the method can be modified to generate layered scaffolds by stacking additional layers of water soluble films on top of one layer of electrospun scaffold and then electro spun an additional time to generate multiple layers of biomaterial.

A large variety of both natural, and synthetic materials may be used for the formation of nanofibrous scaffolds. Some examples of synthetic polymers that can be used are polylactic acid (PLA), polyglycolic acid (PGA), poly-L-lactic acid (PLLA), poly (D, L-lactic-co-glycolic acid) (poly (D, L-lactide-co-glycolide); PLGA), poly (caprolactone) (PCL), diol/di acid-based aliphatic polyester, polyesteramide/polyester-urethane, aliphatic polyester of poly (valerolactone), poly (hydroxybutyrate) and poly (hydroxy valerate). Some natural materials that may be utilized include collagen, fibronectin, alginate, hyaluronic acid, and other such extracellular matrix proteins. In addition, inorganic molecules such as hydroxyapatite, tricalcium phosphate, tetracalcium phosphate, and various other metallic ions and ceramic molecules may be incorporated. All of these components may be utilized by themselves or in tandem with other components. For example, collagen may be combined with polycapralactone and hydroxyapatite to form a composite scaffold.

Other previously utilized and publicly available methods may be used in concert with the methods described in the current invention. For example, the salt leaching method described above may be used. Another potential method that may be utilized involves the incorporation of sodium bicarbonate by dissolving it into the polymer mixture, placing it within the spaces of the soluble and patterned film, or slowly sprinkling it onto the scaffold during scaffold formation. Following formation of the scaffold, the collector, along with the soluble film and the formed scaffold, are placed into citric acid. The citric acid causes the formation of carbon dioxide from the sodium bicarbonate and produces gas pockets that displace the nanofibers within the scaffold, resulting in enhanced porosity.

The potential applications of the present invention are not limited to tissue engineering. Other areas of application may include cosmetics, pharmaceuticals, and retail among others. In one embodiment, a water soluble face mask functionalized with various vitamins and minerals may be prepared for cosmetics applications.

The present invention having been described, the following examples are offered by ways of illustration and are not intended to limit the scope of the present invention.

Example 1

Preparation of PLGA and PCL Membrane Sheets 6 wt % PCL (Mw 70,000~90,000 Da, Sigma Aldrich) and 8 wt % PLGA (Lactic acid:Glycolic acid=82:18, Mw 218 kDa, Evonik, Germany) solutions were dissolved in a mixture of chloroform and methanol (7:3) respectively, and were stirred 800 rpm for 3 hours at room temperature. All electrospinning was performed with an electro spinning machine (ESR200R2D, Nano NC, South Korea) at room temperature at 60% relative humidity. A high voltage of 15.5 kV~16.0 kV with a flow rate of 4.0 ml/hr was used to generate nanofibers with a 25 gauge metal needle. The distance between a collector and polymeric jet solutions was about 13 cm. For preparing the double layered collectors, two water-soluble polymer sheets, embroidery water soluble stabilizer film (EWS) and solvy water soluble stabilizer film (SWS), were purchased from Sulky and Vilene companies, respectively (Table 1). Both polymer sheets were made of polyvinyl alcohol (PVA) and had different patterned structures. To collect patterned porous nanofibrous membrane sheets, electrospun nanofibers collected onto the double layered collectors were placed in distilled water, following which, the water was changed periodically for two days.

TABLE 1

Different collectors leading to different morphologic nanofibrous membrane sheets

| Type of Polymers | Collector Materials |
|---|---|
| PCL | |
| fPCL | Aluminum foil (control) |
| ewsPCL | Embroidery water soluble stabilizer film (EWS)/Aluminum foil |
| swsPCL | Solvy water soluble stabilizer film (SWS)/Aluminum foil |
| PLGA | |
| fPLGA | Aluminum foil (control) |
| ewsPLGA | Embroidery water soluble stabilizer film (EWS)/Aluminum foil |
| swsPLGA | Solvy water soluble stabilizer film (SWS)/Aluminum foil |

Morphological Characterization of Membrane Sheets

Both light microscope (Nikon eclipse TS 100, Japan) and scanning electron microscope (SEM, PHENOM G2 pro series, PHENOM, USA) imaging was used. Each sample was prepared attaching the scaffold using carbon coated tape to a SEM sample stub, and coating with platinum for 60 s in an ion sputter coater (E-1045, HITACHI, Japan) at 15 mA. Scaffolds containing cells were fixed with 4% formaldehyde solution (Sigma Aldrich) for 30 minutes. Samples were dried using a successive dehydration method with at 50, 75, and 100% ethanol.

Figure 2:
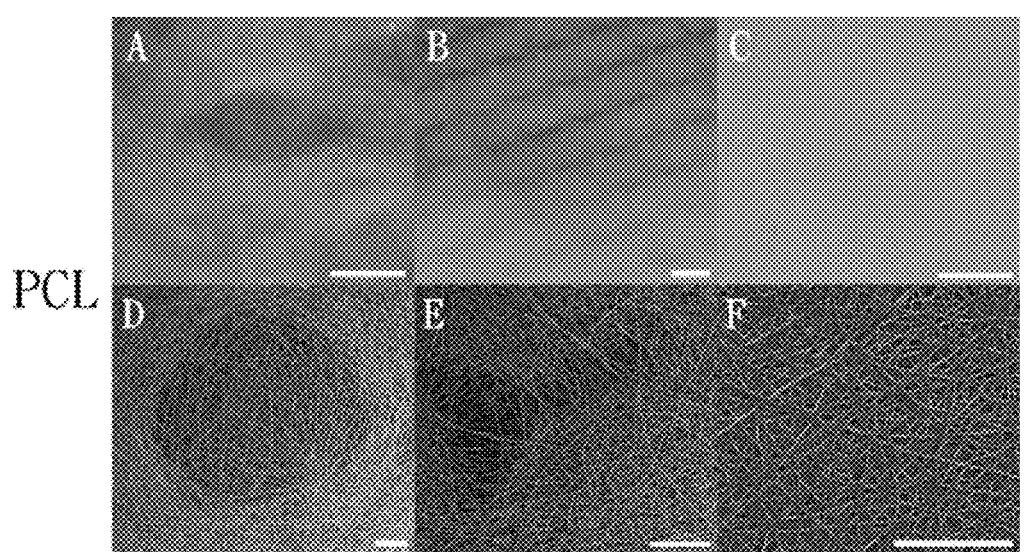
FIG. 2 shows the surface morphology of patterned porous nanofibrous PCL membrane sheets observed by optical microscopy (A-C) and scanning electron microscopy (D-F). (A) and (D) are ewsPCLs. (B) and (E) are swsPCLs. (C) and (F) are ƒPCLs. Upper panel: 500 μm scale bars. Lower panel: 500 μm scale bars.
Figure 3:
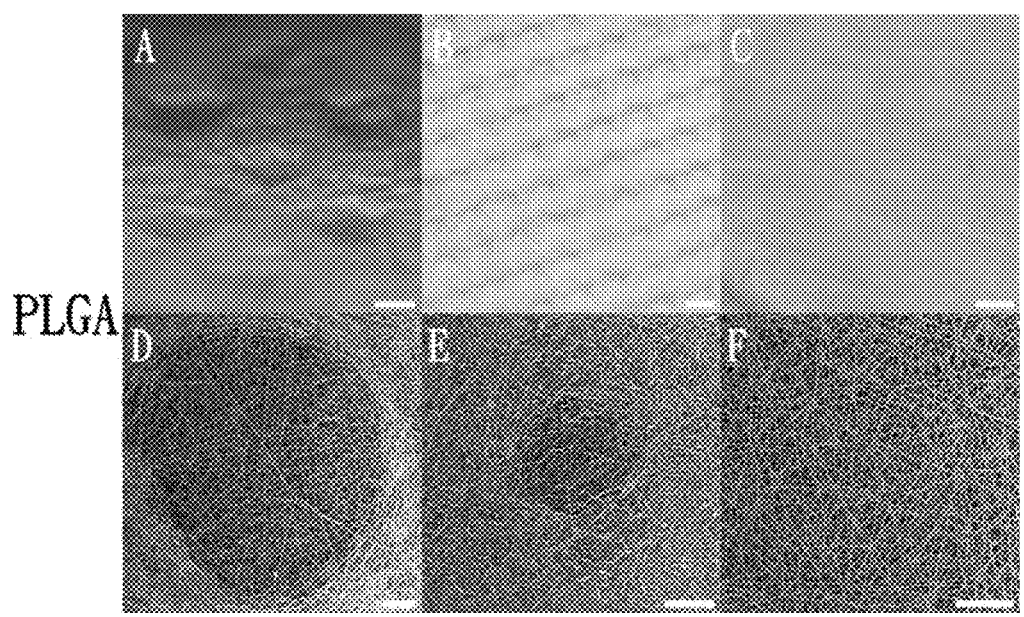
FIG. 3 shows the surface morphology of patterned porous nanofibrous PLGA membrane sheets observed by optical microscopy (A-C) and scanning electron microscopy (D-F). (A) and (D) are ewsPLGAs. (B) and (E) are swsPLGAs. (C) and (F) are ƒPLGAs. Upper panel: 500 μm scale bars. Lower panel: 500 μm scale bars.

In this study, two well-known biodegradable polymers, poly(lactide-co-glycolide) (PLGA) and poly(ε-caprolactone) (PCL), were used to fabricate patterned and porous membrane sheets with this simple-to-use approach. Both biodegradable polymers formed patterned and porous nanofiber membranes on the double layered collectors. For example, on the double layered collectors, the PCL polymers created distinct, patterned structures, whereas the conventional collector apparatus made flat, thick membranes (FIG. 2C). The embroidery water soluble stabilizer film (ewsPCL) gave a much more porous and deep pattern (FIG. 2A) in contrast to the solvy water soluble stabilizer film (swsPCL) (FIG. 2B). In addition to the distinct patterns that can be seen upon gross microscopic observation of the electrospun membranes, the SEM images of each membrane sheet demonstrated that these porous structures exist on the micro level as well, illustrating that the double layered collection system is effective in fabricating the patterned and porous nanofiber membrane sheets (FIGS. 2D and 2E). In contrast to the structures generated with the water soluble stabilizer films, the conventional collector apparatus generated a tightly packed nanofibrous sheet (FIG. 2F). However, the nanofibers made via both the conventional method and using the water soluble stabilizer films measured about 467.2±149.4 nm in diameter on average. As expected, similar patterns on each water soluble stabilizer film were observed in electrospun PLGA membrane sheets as well. It was evident that the electrospun membrane sheets fabricated using the double layered collector exhibited uniformly patterned structures, which were likely to be more favorable to cellular ingrowth under physiological conditions. When deposited onto the water soluble stabilizer films, electrospun PLGA polymers exhibited patterned nanostructures observable using a conventional brightfield microscope (FIGS. 3A and 3B) whereas no patterned structures were observed on the conventional PLGA nanofibrous mat (FIG. 3C). SEM images taken from electrospun PLGA polymers fabricated with the double layered collector indicated that the nanofibers formed similar porous structures due to the patterned water soluble stabilizer films (FIGS. 3D and 3E) as compared to the control (FIG. 3F). Additionally, the diameter of the PLGA nanofibers measured around 571.7±170.9 nm on average irrespective of the type of fabrication method used. Similar techniques with surrogate materials such as lavatory paper, woven fabric, and gauze have been reported to generate patterned structures as well [23]. However, theses insulating substrates are limited in terms of their ability to generate a wide variety of biomimetic scaffolds that are capable of supporting cellular infiltration. Additionally, these insulated substrates are limited in their ability to form a wide variety of different scaffold types. One of the advantages of this method is that the water soluble stabilizer films are easily removed from the desired membrane, leading to the formation of multi-layered structures. This strategy enables us to fabricate multi-layered membranes, which have porous structures for periodontal regeneration. Additionally, pre-existing techniques such as salt leaching, gas foaming, and freeze-drying can be utilized in concert with the double layered technique in order to completely control the porosity of the membranes while eliminating the surrogate materials directly without the use of harsh and non-aqueous solvents.

Example 2

Cellularity of Human Adipose-Derived Stem Cells within the Patterned and Porous Nanofibrous Membrane Sheets After ethylene oxide (EO) gas treatment, membrane sheets were placed at room temperature for two days under a sterilize environment in order to construct membrane-embedded inserts for cellular studies. The membrane-embedded inserts were placed into 70% ethanol solution for 10 minutes and then rinsed with Dulbecco's phosphate buffered saline (DPBS) solution for three times to remove ethanol residuals. Human adipose-derived stem cells (hASC) were isolated from primary culture of the patient's adipose tissue obtained from Korea Cancer Center Hospital under the guide of Institutional Review Board (IRB) at Chung-Ang University. After expanding up to passage 4, 15,000 cells were seeded on the membrane-embedded inserts, and cultured up to 7 days at 37° C. in an atmosphere of 95% humidity and 5% $CO_2$. The culture media consisted of low glucose Dulbecco's modified Eagle's Media (DMEM, Hyclone, USA) containing 1% antibiotic-antimyotic solution (Hyclone) supplemented with Fetal Bovine Serum (FBS, Hyclone). To measure the total cellular proliferation activity within each sample, a 10% working solution of alamar blue 10% (Invitrogen, USA) was made by diluting alamar blue with complete cell culture media at a ratio of 9 to 1. Following this, each insert was introduced to the working alamar blue solution and incubated for 4 hrs. Fluorescence was measured at 570 nm (Ex 560 nm/Em 590 nm) with a microplate reader (Synergy H1 Hybrid Multi-mode Microplate Reader, Bio-tek, USA). Hematoxylin and eosin (H&E) staining was also utilized for observing the morphological pattern in each scaffold.

Statistical Analysis

All experiments were performed four independent times, and the total cellular proliferation activities were expressed as mean±standard deviation. One-way analysis of variance and Tukey multiple comparison test were employed to determine significant differences between pairs. SPSS 15.0 software (SPSS Inc., IL) was used to perform statistical analysis. $p<0.05$ was considered statistically significant.

Figure 4:
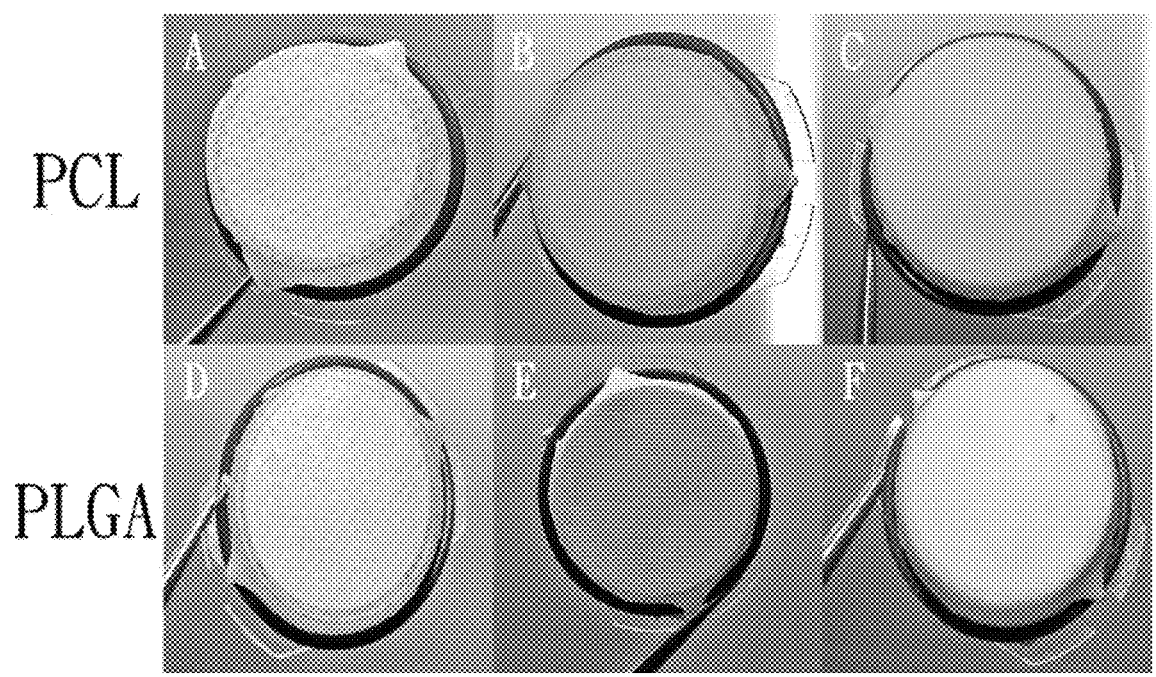
FIG. 4 shows images of fabricated patterned and porous nanofibrous membrane sheets (A: ewsPCL; B: swsPCL; D: ewsPLGA; and E: swsPLGA) and nanofibrous membrane obtained from traditional electrospinning method (C: ƒPCL; and F: ƒPLGA).
Figure 5:
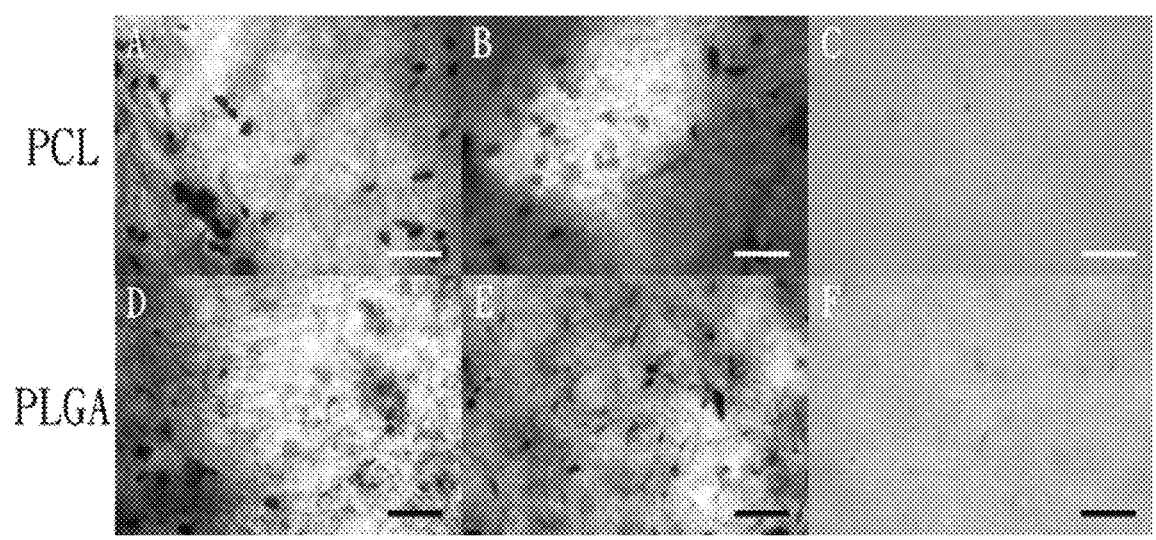
FIG. 5 shows images of human adipose-derived stem cells (hASCs) seeded on PCL and PLGA patterned porous nanofibrous membrane sheets. Hematoxylin-Eosin (H&E) staining were performed after seeding onto each membrane sheet. (A) ewsPCL, (B) swsPCL, (C) ƒPCL, (D) ewsPLGA, (E) swsPLGA, and (F) ƒPLGA. All scale bars indicate 100 μm.
Figure 6A:
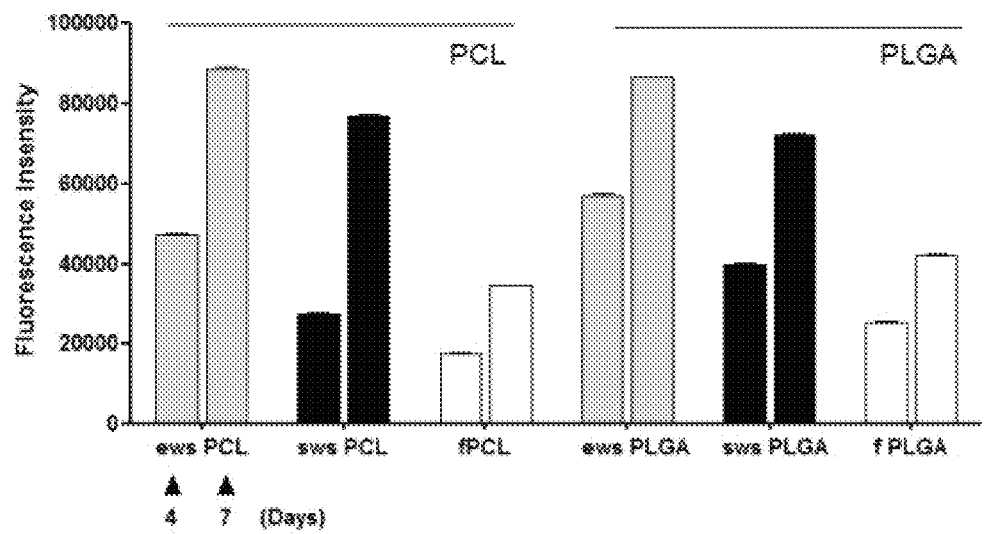
FIGS. 6A and 6B show total cellular proliferation activity of hASCs after 7 days cultivation. (6A) Absolute fluorescence activity. (6B) Normalized values. Each value is expressed as mean±standard deviation relative to controls (ƒPCL and ƒPLGA) (dashed line) for all time points. ($p<0.05$).
Figure 6B:
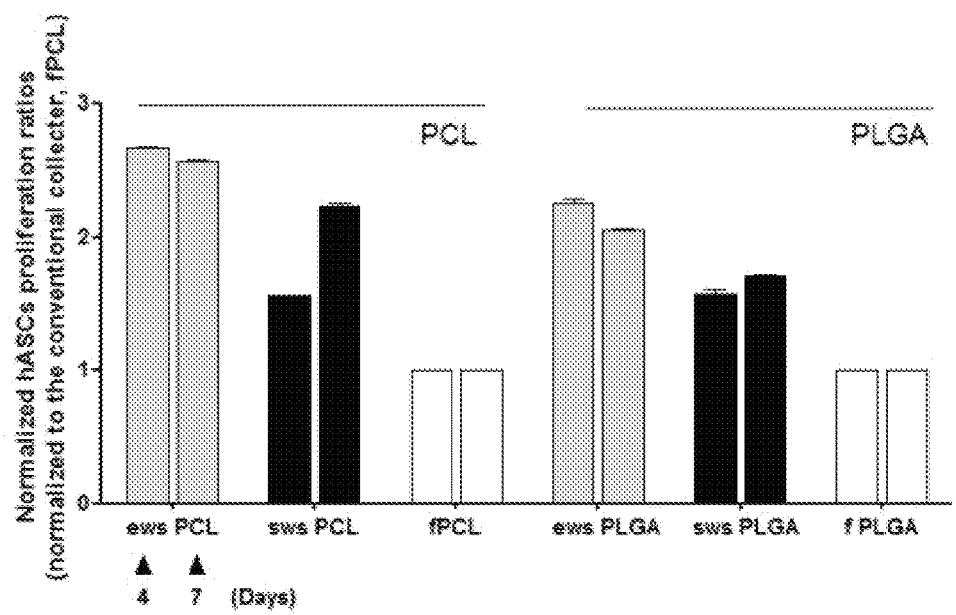
Figure 7:
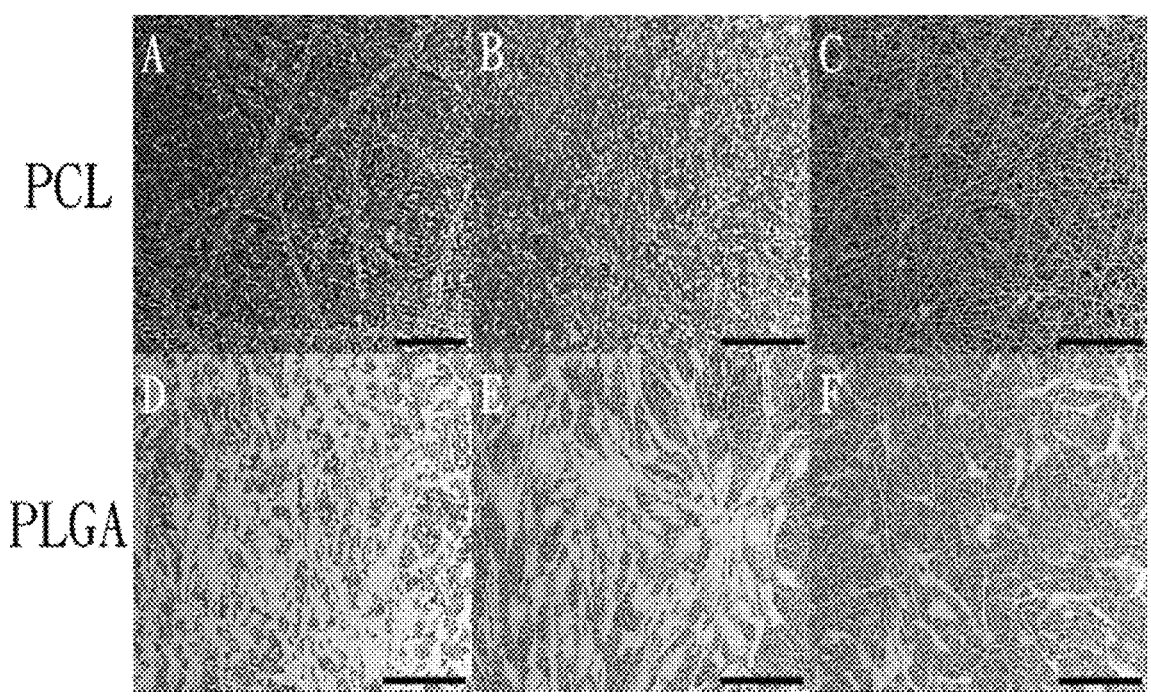
FIG. 7 shows representative SEM image of hASCs seeded on the patterned porous nanofibrous PCL and PLGA membrane sheets after 7 days. Upper panel: PCL membranes. Lower panel: PLGA membranes. All scale bars indicate 150 μm.

In order to evaluate the ability of the fabricated patterned nanofiberous membrane sheets to support cellular ingrowth, human adipose-derived stem cells (hASCs) were seeded, and stained using hematoxylin and eosin (H&E) (FIG. 4). hASCs are a well-known stem cell source for regenerative applications and it has been demonstrated that they hold similar and sometimes superior regenerative potential when compared to bone marrow-derived mesenchymal stem cells [24]. hASCs are obtainable in a large quantities during liposuction procedures, enabling the autologous implantation of large quantities of hASCs. hASCs seeded on the patterned and porous nanofiberous membrane sheets grew directly into the surface pores, and attached on the inner space of the sheets. After seeding on each membrane, the cellular ingrowth of hASCs was assessed with H&E staining. After 24 hours of incubation, cells were fixed and stained as described above. Overall, significantly more cells were observed on the patterned, porous nanofiber membranes. Both the electrospun PCL and PLGA polymers with uniformly patterned nanofibrous structures allowed enhanced cellular ingrowth of hASCs (FIG. 5). H&E staining of the membrane sheets demonstrated that cells attached onto fabricated membranes more efficiently as compared to the control ƒPCL membrane in FIG. 5C. In the case of electrospun PLGA polymers, ewsPLGA and swsPLGA membrane sheets exhibited improved cell attachment, implying that the patterned and porous nanofiber membranes may support better cellular ingrowth than on conventionally fabricated membranes (FIGS. 5D, 5E, and 5F). To confirm enhanced cellular ingrowth on fabricated membranes, the cellularity of hASCs was examined using a quantitative alamar blue assay. In all patterned, porous membrane sheets, hASCs proliferated faster than hASCs seeded on control membrane sheets for the same cultivation periods. The difference in hASCs cellular ingrowth on the patterned, porous nanofiber scaffolds was statistically significant in comparison to hASCs seeded on scaffolds fabricated with conventional methods for all time points (FIG. 6). The absolute fluorescent activity of hASCs on the patterned and porous nanofiber membrane sheets was greater than in the control group, showing that both the fabricated PLGA and PCL membrane sheets supported hASC attachment and cell proliferation. SEM images also indicated that more cells occupied the patterned and porous membrane sheets, demonstrating that the patterned and porous nanofibers were a more conducive environment for cellular proliferation than that of the control membranes (FIG. 7). One interesting observation was that hASCs seeded on electrospun PCL membrane sheets were round in shape, whereas these cells were fibroblast-like on PLGA membrane sheets. A number of studies have been reported that biomaterial properties including chemical structures and surface properties can modulate cell orientation, motility, adhesion and shape [25, 26]. Therefore, our finding is that hASC cellular morphology seeded on different nanofibrous membrane sheets may manifest as a result of different chemical properties of both polymers, as cellular shape was not irrespective of mode of preparation.

Example 3

Preparation of PCL on a Three-Dimensional Pouch

Figure 8:
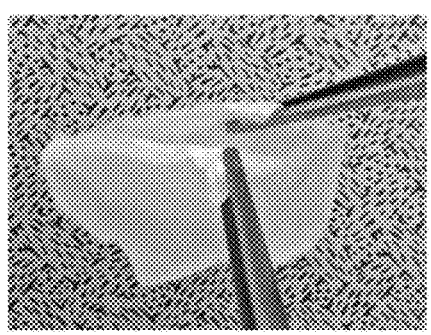
FIG. 8 depicts a three dimensional pouch made by combining two water soluble films, electrospinning PCL on both sides, and then dissolving the film(s) in water. (A) Pouch made by combining two water soluble films and electrospinning on both sides, then dissolving the film. (B) Opening up the pouch to demonstrate that it has a hollow structure. (C) Close up depiction of the inside of the pouch.
Figure 8:
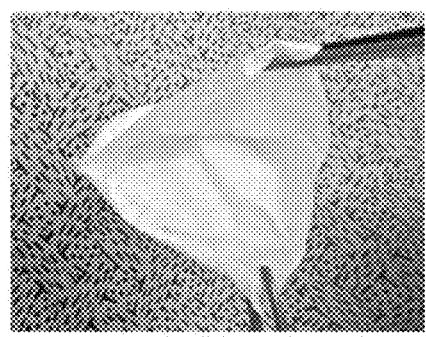
Figure 8:
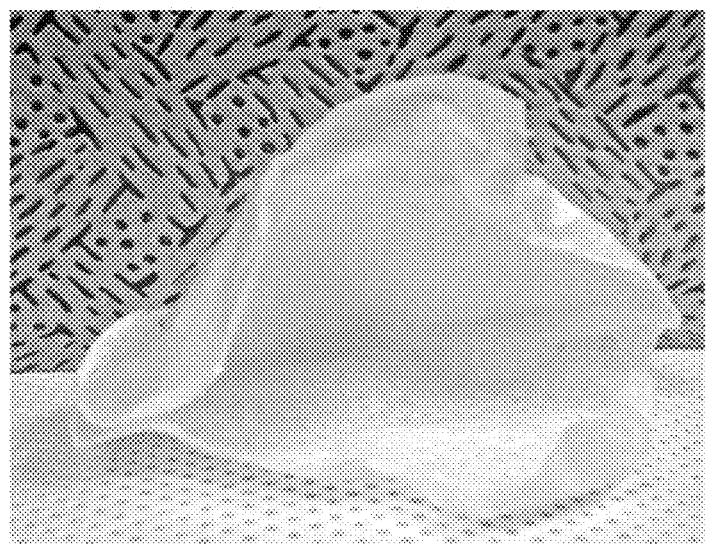
Figure 9:
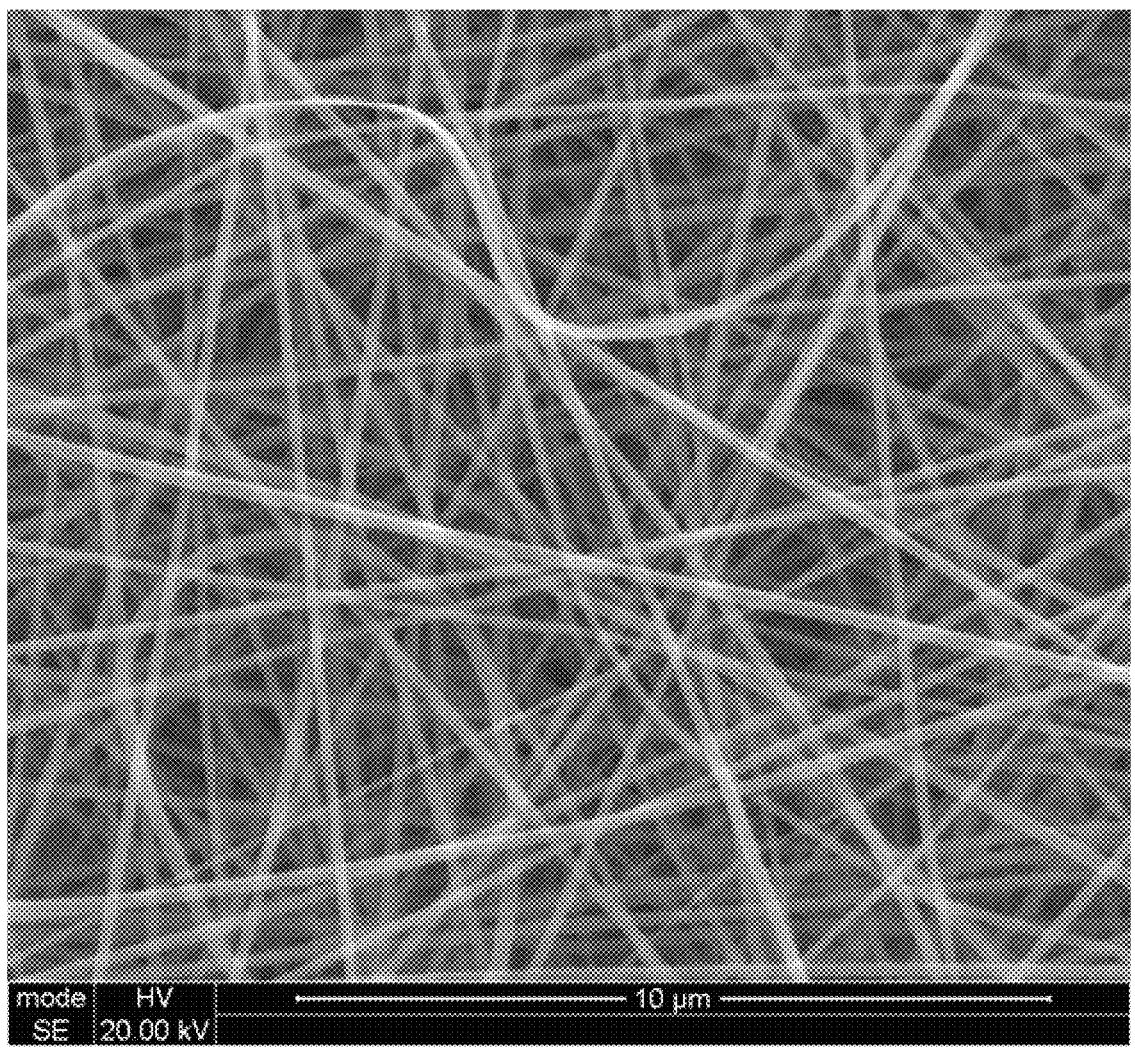
FIG. 9 is a zoomed-in image of electrospun collagen nanofibers.
Figure 10:
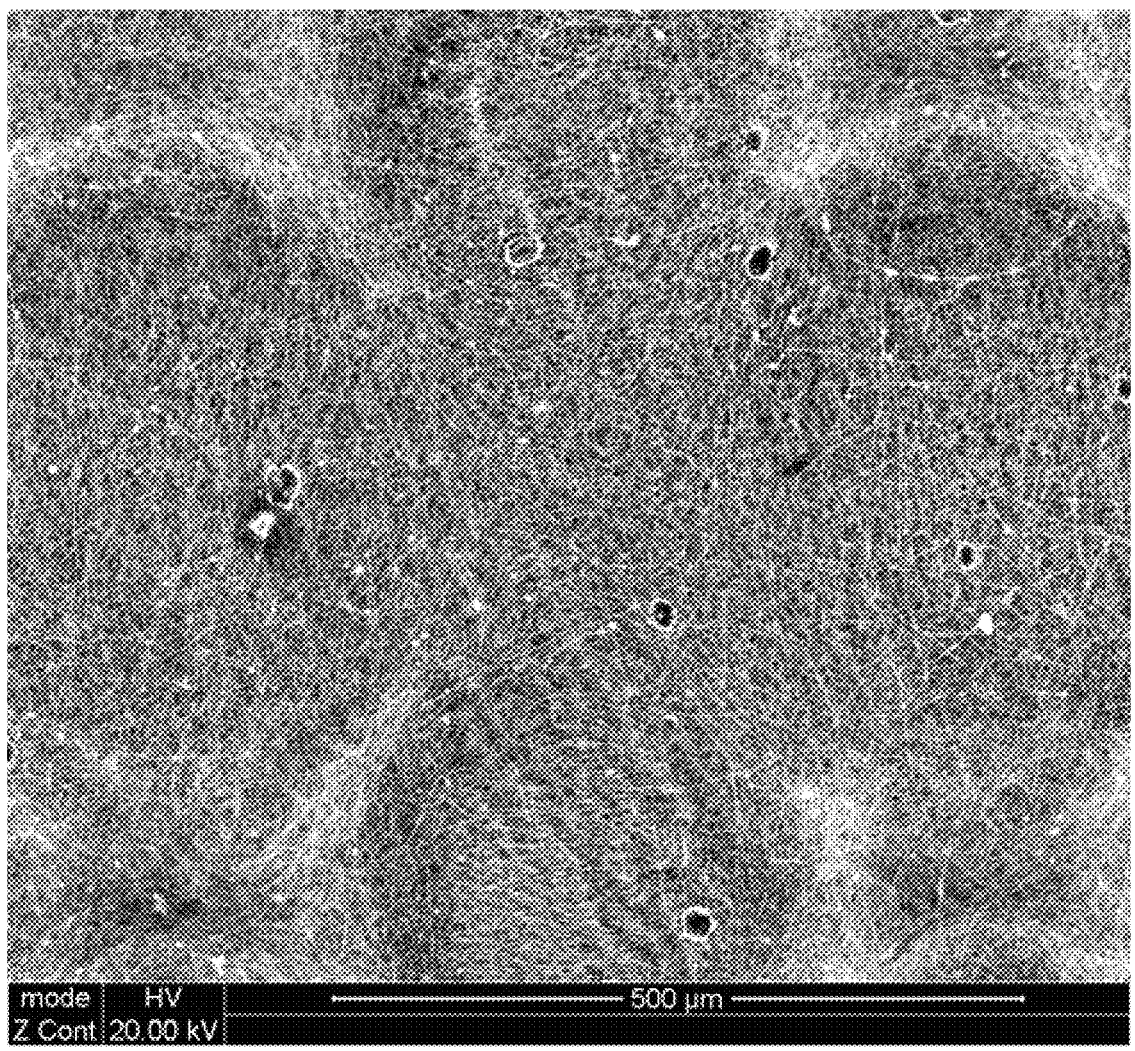
FIG. 10 is an image displaying formation of patterned electrospun collagen nanofiber macrostructure.
Figure 11:
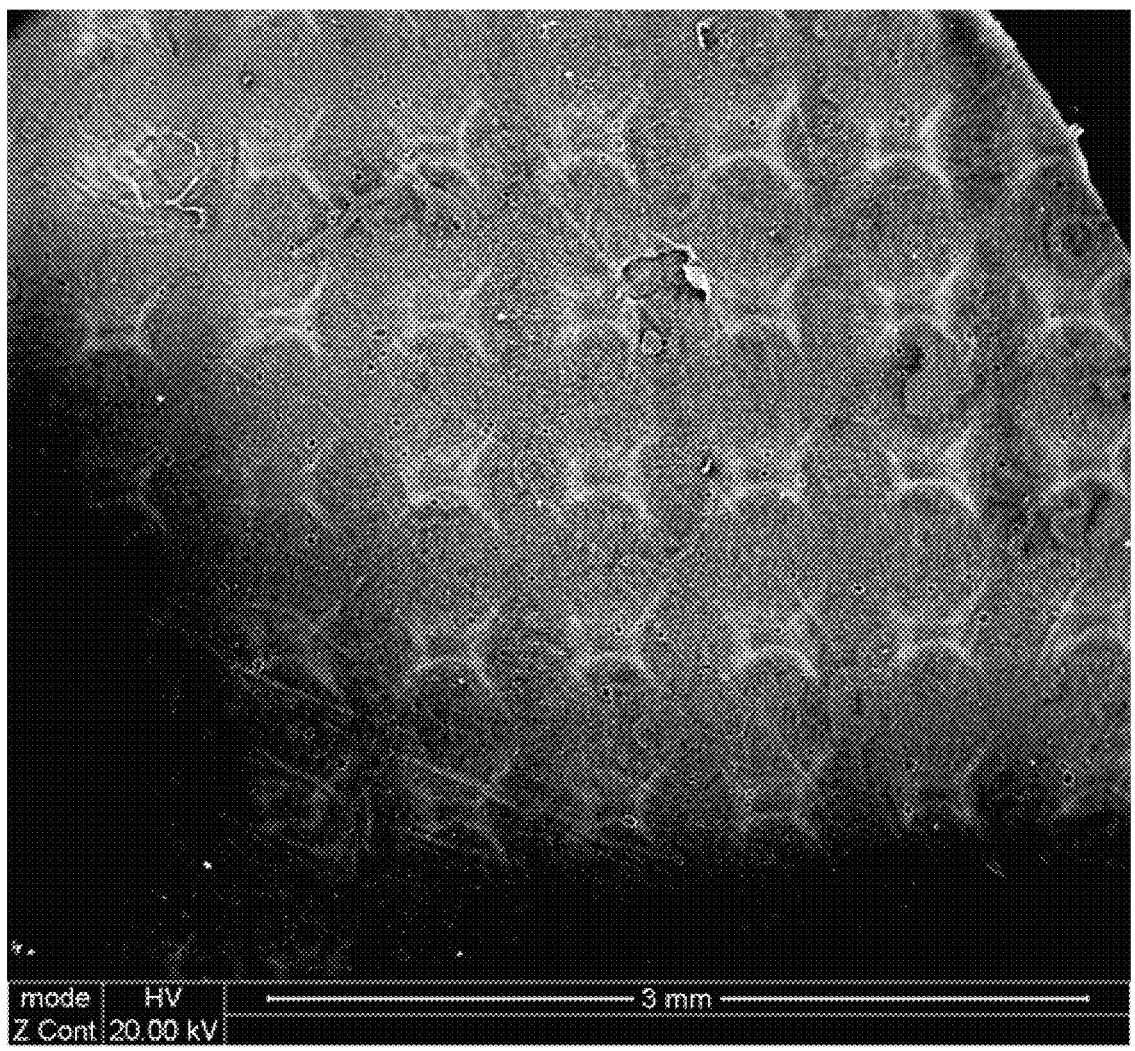
FIG. 11 is a zoomed-out image demonstrating patterned macrostructure of electrospun collagen nanofibers.

A three dimensional pouch made by combining two water soluble films, electrospinning PCL on both sides, and then dissolving the film(s) in water (FIG. 8).

Although the invention has been explained in relation to its preferred embodiment, it is to be understood that many other possible modifications and variations can be made without departing from the spirit and scope of the invention as herein described.

REFERENCES

[1] Tsang V L, Bhatia S N. Three-dimensional tissue fabrication. Advanced drug delivery reviews 2004; 56:1635-47.
[2] Hollister S J. Porous scaffold design for tissue engineering. Nature materials 2005; 4:518-24.
[3] Karageorgiou V, Kaplan D. Porosity of 3D biomaterial scaffolds and osteogenesis. Biomaterials 2005; 26:5474-91.
[4] Yang S, Leong K F, Du Z, Chua C K. The design of scaffolds for use in tissue engineering. Part I. Traditional factors. Tissue engineering 2001; 7:679-89.
[5] Mikos A G, Temenoff J S. Formation of highly porous biodegradable scaffolds for tissue engineering2000.
[6] Tang Z G, Black R A, Curran J M, Hunt J A, Rhodes N P, Williams D F. Surface properties and biocompatibility of solvent-cast poly[-caprolactone] films. Biomaterials 2004; 25:4741-8.
[7] Lu L, Peter S J, Lyman M D, Lai H L, Leite S M, Tamada J A, et al. In vitro degradation of porous poly(L-lactic acid) foams. Biomaterials 2000; 21:1595-605.
[8] Nam Y S, Yoon J J, Park T G. A novel fabrication method of macroporous biodegradable polymer scaffolds using gas foaming salt as a porogen additive. Journal of biomedical materials research 2000; 53:1-7.

[9] Whang K, Thomas C H, Healy K E, Nuber G. A novel method to fabricate bioabsorbable scaffolds. Polymer 1995; 36:837-42.

[10] Peltola S M, Melchels F P, Grijpma D W, Kellomaki M. A review of rapid prototyping techniques for tissue engineering purposes. Annals of medicine 2008; 40:268-80.

[11] Teo W E, Ramakrishna S. A review on electrospinning design and nanofibre assemblies. Nanotechnology 2006; 17:R89-R106.

[12] Wright L D, Andric T, Freeman J W. Utilizing NaCl to increase the porosity of electrospun materials. Materials Science and Engineering: C 2011; 31:30-6.

[13] Buser D, Dula K, Belser U, Hirt H P, Berthold H. Localized ridge augmentation using guided bone regeneration. 1. Surgical procedure in the maxilla. Int J Periodontics Restorative Dent 1993; 13:29-45.

[14] Nyman S, Lindhe J, Karring T, Rylander H. New attachment following surgical treatment of human periodontal disease. J Clin Periodontol 1982; 9:290-6.

[15] Gottlow J, Nyman S, Karring T, Lindhe J. New attachment formation as the result of controlled tissue regeneration. J Clin Periodontol 1984; 11:494-503.

[16] Dahlin C, Linde A, Gottlow J, Nyman S. Healing of bone defects by guided tissue regeneration. Plast Reconstr Surg 1988; 81:672-6.

[17] Murphy K G. Postoperative healing complications associated with Gore-Tex Periodontal Material. Part I. Incidence and characterization. Int J Periodontics Restorative Dent 1995; 15:363-75.

[18] Simion M, Scarano A, Gionso L, Piattelli A. Guided bone regeneration using resorbable and nonresorbable membranes: a comparative histologic study in humans. Int J Oral Maxillofac Implants 1996; 11:735-42.

[19] Fujihara K, Kotaki M, Ramakrishna S. Guided bone regeneration membrane made of polycaprolactone/calcium carbonate composite nano-fibers. Biomaterials 2005; 26:4139-47.

[20] Taguchi Y, Amizuka N, Nakadate M, Ohnishi H, Fujii N, Oda K, et al. A histological evaluation for guided bone regeneration induced by a collagenous membrane. Biomaterials 2005; 26:6158-66.

[21] Scantlebury T V. 1982-1992: a decade of technology development for guided tissue regeneration. J Periodontol 1993; 64:1129-37.

[22] Gentile P, Chiono V, Tonda-Turo C, Ferreira A M, Ciardelli G. Polymeric membranes for guided bone regeneration. Biotechnology Journal 2011; 6:1187-97.

[23] Zhao S, Zhou Q, Long Y Z, Sun G H, Zhang Y. Nanofibrous patterns by direct electrospinning of nanofibers onto topographically structured non-conductive substrates. Nanoscale 2013; 5:4993-5000.

[24] Gimble J M, Katz A J, Bunnell B A. Adipose-derived stem cells for regenerative medicine. Circulation research 2007; 100:1249-60.

[25] Kulangara K, Leong K W. Substrate topography shapes cell function. Soft Matter 2009; 5:4072-6.

[26] Schwarz U S, Bischofs I B. Physical determinants of cell organization in soft media. Med Eng Phys 2005; 27:763-72.

[27] Kim T G, Chung H J and Park T G. Macroporous and nanofibrous hyaluronic acid/collagen hybrid scaffold fabricated by concurrent electrospinning and deposition/leaching of salt particles. Acta Biomater. 2008; 4:1611-9.

[28] Li J, He A, Zheng J and Han C C. Gelatin and gelatin-hyaluronic acid nanofibrous membranes produced by electrospinning of their aqueous solutions. Biomacromolecules. 2006; 7:2243-7.

[29] Buttafoco L, Kolkman N G, Engbers-Buijtenhuijs P, Poot A A, Dijkstra P J, Vermes I and Feijen J. Electrospinning of collagen and elastin for tissue engineering applications. Biomaterials. 2006; 27:724-34.

[30] Matthews J A, Wnek G E, Simpson D G and Bowlin G L. Electrospinning of collagen nanofibers. Biomacromolecules. 2002; 3:232-8.

[31] Fischer R L, McCoy M G and Grant S A. Electrospinning collagen and hyaluronic acid nanofiber meshes. J Mater Sci Mater Med. 2012; 23:1645-54.

[32] Elamparithi A, Punnoose A M and Kuruvilla S. Electrospun type 1 collagen matrices preserving native ultrastructure using benign binary solvent for cardiac tissue engineering. Artif Cells Nanomed Biotechnol. 2016; 44:1318-25.

[33] Dong B, Arnoult O, Smith M E and Wnek G E. Electrospinning of collagen nanofiber scaffolds from benign solvents. Macromol Rapid Commun. 2009; 30:539-42.

The invention claimed is:

1. A method of producing a nanofibrous polymer membrane sheet, the method comprising:
providing a syringe;
providing a solution comprising a natural or synthetic polymer or in combination thereof;
adding the solution comprising the natural or synthetic polymer or in combination thereof into the syringe;
providing a collector having a foil attached around the collector;
providing a water soluble film that is mounted on the foil;
providing a voltage source comprising a positive charge and a ground;
electrically connecting the positive charge to the syringe and the collector to the ground, and generating a voltage differential;
applying a voltage to the collector and the syringe in response to generating the voltage differential in between the syringe and the collector;
depositing the solution comprising the natural or synthetic polymer or in-a combination thereof on the water soluble film;
spinning the collector;
providing water;
producing a nanofibrous polymer membrane sheet by dissolving the water soluble film in the water; and
isolating the nanofibrous polymer membrane sheet.

2. The method according to claim 1, wherein the water soluble film mounted on the foil comprises a water soluble polymer.

3. The method according to claim 2, wherein the water soluble polymer film is embroidery water soluble stabilizer film or solvy water soluble stabilizer film.

4. The method according to claim 3, wherein the water soluble polymer film comprises polyvinyl alcohol.

5. The method according to claim 1, wherein the natural polymer in the syringe is selected from the group consisting of collagen, fibronectin, alginate, hyaluronic acid and other extracellular matrix proteins and the synthetic polymer in the syringe is selected from the group consisting of polylactic acid (PLA), polyglycolic acid (PGA), poly-L-lactic acid (PLLA), poly(D,L-lactic-co-glycolic acid) (PLGA), poly(caprolactone) (PCL), aliphatic polyester of poly(valeroactone), poly(hydroxybutyrate) and poly(hydroxy valerate).

6. The method according to claim 1, wherein the polymer in the syringe is a natural polymer.

7. The method according to claim 6, wherein the natural polymer is selected from the group consisting of collagen, fibronectin, alginate, and hyaluronic acid.

8. The method according to claim 1, wherein the solution comprising a natural or synthetic polymer or a combination thereof in the syringe further comprises inorganic molecules selected from the group consisting of salt, hydroxyapatite, tricalcium phosphate, and tetracalcium phosphate.

9. The method according to claim 1, wherein the nanofibrous membrane sheets are further seeded with cells.

10. The method according to claim 9, wherein the cells attached on the nanofibrous membrane sheets are human adipose-derived stem cells (hASCs), fibroblast stem cells, or mesenchymal stem cells.

11. A method of producing multiple nanofibrous polymer membrane sheets comprising:
   producing a plurality of nanofibrous polymer membrane sheets by using the method of claim 1; and
   stacking the plurality of nanofibrous polymer membrane sheets on one another.

\* \* \* \* \*